(12) United States Patent
Feussner et al.

(10) Patent No.: US 7,179,626 B1
(45) Date of Patent: Feb. 20, 2007

(54) 11-ARACHIDONATE-LIPOXYGENASE MUTANTS

(75) Inventors: Ivo Feussner, Halle (DE); Ellen Hornung, Quedlinburg (DE); Sabine Rosahl, Halle (DE)

(73) Assignee: Institut fur Pflanzenbiochemie-IPB, Halle (DE)

( * ) Notice: Subject to any disclaimer, the term of this patent is extended or adjusted under 35 U.S.C. 154(b) by 434 days.

(21) Appl. No.: 10/030,464

(22) PCT Filed: Jul. 10, 2000

(86) PCT No.: PCT/EP00/06539

§ 371 (c)(1),
(2), (4) Date: May 22, 2002

(87) PCT Pub. No.: WO01/04323

PCT Pub. Date: Jan. 18, 2001

(30) Foreign Application Priority Data

Jul. 8, 1999 (DE) .................... 199 31 819

(51) Int. Cl.
C12N 9/02 (2006.01)
C12N 1/20 (2006.01)
C12N 15/00 (2006.01)
C12P 21/04 (2006.01)
C07H 21/04 (2006.01)

(52) U.S. Cl. .............. 435/189; 435/440; 435/252.3; 435/320.1; 435/69.1; 435/71.1; 536/23.2; 536/23.6

(58) Field of Classification Search ............... 435/189, 435/252.3, 320.1, 71.1, 69.1, 440, 4, 25, 435/6; 536/23.2, 23.7, 23.6
See application file for complete search history.

(56) References Cited

FOREIGN PATENT DOCUMENTS

WO    WO 00/60093 A    10/2000

OTHER PUBLICATIONS

Gan et al. Defining the arachidonic acid binding site of human 15-lipoxygenase. Molecular modeling and mutagenesis. J Biol Chem. Oct. 11, 1996;271(41):25412-8.*

(Continued)

*Primary Examiner*—Tekchand Saidha
*Assistant Examiner*—Yong D. Pak
(74) *Attorney, Agent, or Firm*—Leydig, Voit & Mayer, Ltd.

(57) ABSTRACT

A method for producing a plant lipoxygenase (LOX) with modified positional specificity toward arachidonic acid and its use for hydroperoxylation of arachidonic acid. The LOX makes it possible to produce for the first time (11S,14Z,12E, 8Z,5Z)-11-hydroperoxy-14,12,8,5-eicosatetraenic acids on a large scale. To this end, arachidonic acid is incubated as substrate with the LOX under appropriate conditions. Hydroperoxylation of the arachidonic acid is then effected, preferably at position 11, with secondary products which are hydroperoxylated at position 8, at position 5, or at positions 11 and 8 and 5.

6 Claims, 3 Drawing Sheets

OTHER PUBLICATIONS

Geerts et al. Expression of lipoxygenase in wounded tubers of *Solanum tuberosum*L. Plant Physiol. May, 1994;105(1):269-77.*

Sequence Alignment.*

ExPASy: lipoxygenase*

Di Marzo et al., "Biosynthesis, structure and biological activity of hydroxyeicosatetaenoic acids in *Hydra vulgaris*," *Biochemical Journal*, 295 (1), 23-29 (Oct. 1, 1993).

Di Marzo et al., "Polyunsaturated-fatty-acid oxidation in Hydra: Regioselectivity, substrate-dependent enantioselectivity and possible biological role," *Biochemical Journal*, 300 (2), 501-507 (Jun. 1, 1994).

Feussner et al., "Lipoxygenase catalyzed oxygenation of lipids," *FETT*, 100 (4-5), 146-152 (May, 1998).

Hawkins et al., "Eggs of the sea urchin, *Stronngylocentrotus purpuratus*, contain a prominent (11R) and (12R) lipoxygenase activity," *J. Biol. Chem.*, 262 (16), 7629-7634 (Jun. 5, 1987).

Hawkins et al., "Resolution of enantiomers of hydroxyeicosatetraenoate derivatives by chiral phase high-pressure liquid chromatography," *Analytical Biochemistry*, 173 (2), 456-462 (Sep. 1988).

Hawkins et al., "Mechanisms of biosynthesis of 11R- and 12R-hydroxyeicosatetraenoic acids by eggs of the sea urchin *Stronnsylocentrotus purpuratus*," *FEBS Letters*, 247 (1), 9-12 (Apr. 10, 1989).

Hornung et al., "Conversion of cucumber linoleate 13-lipoxygenase to a 9-lipoxygenating species by site-directed mutagenesis," *PNAS USA*, 96 (7), 4192-4197 (Mar. 30, 1999).

Kuenn et al., "Analysis of the stereochemistry of lipoxygenase-derived hydroxypolyenoic fatty acids by means of chiral phase high-pressure liquid chromatography," *Analytical Biochemistry*, 160 (1), 24-34 (Jan. 1987).

Leitz et al., "Enantiospecific synthesis of bioactive hydroxyeicosatetraenoic acids (HETEs) in *Hydra magnipapillata*," *Biochimica et Biophysica Acta*, 1213 (2), 215-223 (Jul. 14, 1994).

Mulliez et al., "5-Lipoxygenase from potato tubers improved purification and physicochemical characteristics," *Biochimica et Biophysica Acta*, 916 (1), 13-23 (1987).

Porter et al., "The resolution of racemic hydroperoxides: a chromatography-based separation of perketals derived from arachidonic, linoleic, and oleic acid hydroperoxides," *Chemical Research in Toxicology*, 3 (3), 236-243 (May/Jun. 1990).

Reddy et al., "11-Hydroperoxyeicosatetraenoic acid is the major dioxygenation product of lipoxygenase isolated from hairy root cultures of *Solanum tuberosum*," *Biochemical and Biophysical Research Communications*, 189 (3), 1349-1352 (Dec. 30, 1992).

Reddy et al., "Mechanism of formation of leukotrienes and lipoxins from arachidonic acid catalyzed by homogenous lipoxygenase from potato tubers," in *Advances in Prostaglandin, Thromboxane and Leukotriene Research*, vol. 19, pp. 133-136, B. Samuelsson et al., eds., Raven Press Ltd., New York (1989).

Van Zadelhoff et al., "With anandamine as substrate plant 5-lipoxygenases behave like 11-lipoxygenases," *Biochemical and Biophysical Research Communications*, 248 (1), 33-38 (Jul. 9, 1998).

* cited by examiner

```
  1  QIVGGLIGGH HDSKKVKGTV VMMKKNALDF TDLAGSLTDK IFEALGQKVS FQLISSVQSD
 61  PANGLQGKHS NPAYLENFLF TLTPLAAGET AFGVTFDWNE EFGVPGAFII KNTHINEFFL
121  KSLTLEDVPN HGKVHFVCNS WVYPSFRYKS DRIFFANQPY LPSETPELLR KYRENELLTL
181  RGDGTGKREA WDRIYDYDVY NDLGNPDQGE QNVRTTLGGS ADYPYPRRGR TGRPPTRTDP
241  KSESRIPLIL SLDIYVPRDE RFGHLKMSDF LTYALKSIVQ FILPELHALF DGTPNEFDSF
301  EDVLRLYEGG IKLPQGPLFK ALTAAIPLEM MKELLRTDGE GILRFPTPLV IKDSKTAWRT
361  DEEFAREMLA GVNPIIISRL QEFPPKSKLD PEAYGNQNST ITAEHIEDKL DGLTVDEAMN
421  NNKLFILNHH DVLIPYLRRI NTTTTKTYAS RTLLFLQDNG SLKPLAIELS LPHPDGDQFG
481  VISKVYTPSD QGVESSIWQL AKAYVAVNDS GVHQLISHWL NTHAVIEPFV IATNRQLSVL
541  HPIHKLLYPH FRDTMNINAM ARQILINAGG VLESTVFPSK FAMEMSAVVY KDWVFPDQAL
601  PADLVKRGVA VEDSSSPHGV RLLIEDYPYA VDGLEIWSAI KSWVTDYCSF YYGSDEEILK
661  DNELQAWWKE LREVGHGDKK NEPWWPEMET PQELIDSCTT IIWIASALHA AVNFGQYPYA
721  GYLPNRPTVS RRFMPEPGTP EYEELKKNPD KAFLKTITAQ LQTLLGVSLI EILSRHTTDE
781  IYLGQRESPE WTKDKEPLAA FDKFGKKLTD IEKQIIQRNG DNILTNRSGP VNAPYTLLFP
841  TSEGGLTGKG IPNSVSI

Primer1: GCT GGT GGG GTT CTT GAG AGT ACA TTC TTT CCT TCG AAA TTT GCC
 ATG GAA ATG TCA GCT G Primer2: CAG CGT ACA TTT CCA TGG CAA ATT TCG AAG GAA AGA ATG TAC TCT
 CAA GAA CCC CAC CAG C
```

Fig. 3

11-ARACHIDONATE-LIPOXYGENASE MUTANTS

The present invention relates to a method for producing a plant lipoxygenase with modified positional specificity and to the lipoxygenase obtained by said method and to the use thereof for the hydroperoxylation of arachidonic acid at carbon atom 11.

Lipoxygenases (LOXs, linolic acid: oxygen oxidoreductase; EC.1.13.11.12; LOXs) are widely distributed in the plant and animal kingdom (Siedow, J. N. (1991) Ann. Rev. Plant Physiol. Plant Mol. Biol. 42, 145–188; Yamamoto, S. (1992) Biochim. Biophys. Acta 1128, 117–131). These enzymes constitute a family of iron-containing dioxygenases that catalyze a region- (or position-) and stereo-selective oxygenation of polyenoic fatty acids to hydroperoxy derivatives (Rosahl, S. (1996) Z. Naturforsch. 51c, 123–138). In mammals, LOXs are classified according to their specificity for specific positions during arachidonic acid oxygenation (Yamamoto, S. (1992) Biochim. Biophys. Acta 1128, 117–131; Schewe, T., Rapaport, S. M. & Kühn, H. (1986) Adv. Enzymol. Mol. Biol 58, 191–272). 15-, 12-, 8- and 5-LOXs have so far been isolated here. LOXs which effect the insertion of oxygen at positions 9 and 11, respectively, on the carbon skeleton of arachidonic acid have not been known yet (Yamamoto, S. (1992) Biochim. Biophys. Acta 1128, 117–131). Since arachidonic acid either is not present in higher plants or is only present in small amounts as a constituent of storage lipids, plant LOXs are classified as 9- and 13-LOXs. This nomenclature is derived from the position at which oxygenation takes place in linolic acid (LA) (Gardner, H. W. (1991) Biochim. Biophys. Acta 1084, 221–239). Recently, a more comprehensive classification of plant LOXs has been proposed based on a comparison of the primary structures (Shibata, D. & Axelrod, B. (1995) J. Lipid Mediators Cell Signal. 12, 213–228). The specificity of a LOX for a specific position is the result of two catalytic partial reactions:

(i)

Regio- and stereospecific hydrogen removal; in fatty acids containing several double bonds (such as linolenic acid, arachidonic acid, or eicosapentaenoic acid), hydrogen removal is possible at various positions.

(ii)

Figure 1:
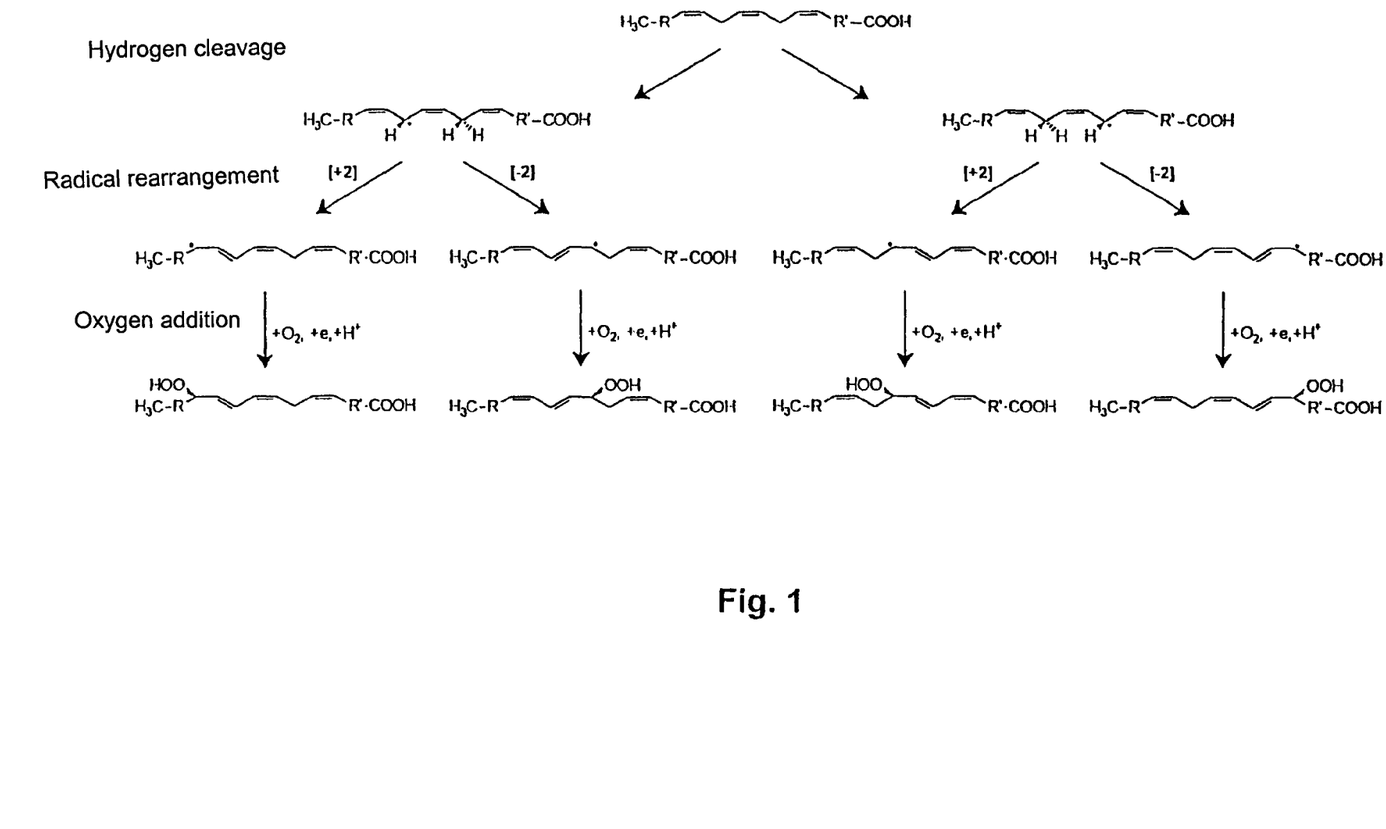
FIG. 1 shows the specificity of a LOX reaction with substrates containing two allylic methylenes.

Regio- and stereospecific oxygen insertion (oxygen can be inserted at various positions (either at the +2 or −2 position)) (cf. FIG. 1). Thus, a fatty acid containing three double-allylic methylenes, such as arachidonic acid, can be oxygenated by a LOX to six regioisomeric hydroperoxy derivatives (HPETEs), namely 15- and 11-HPETE (these originate from the removal of hydrogen at position C-13), 12- and 8-HPETE (these originate from hydrogen removal at position C-10) and 9- and 5-HPETE (these originate from hydrogen removal at position C-7). Experiments on mammalian 12- and 15-LOXs indicated that the position of hydrogen removal can be altered when critical amino acids are changed by directed mutagenesis (Borngräber, S., Kuban, R. J., Anton, M. & Kühn, H. (1996) J. Mol. Biol. 264, 1145–1153; Sloane, D. L., Leung, R., Craik, C. S. & Sigal, E (1991) Nature 354, 149–152). Attempts to alter the LOX reactivity from a +2 to a −2 rearrangement or vice versa (e.g., conversion of a linoleate 13-LOX to a 9-LOX) by directed mutagenesis have recently been successful (Hornung, E., Walther, M., Kühn, H. & Feussner, I. (1999) Proc. Natl. Acad. Sci. USA 96, 4192–4197).

It has been the object of the present invention to indicate a method for providing a LOX with a desired C-11 positional specificity in arachidonic acid.

This problem is solved according to the invention by a method in which at least one amino acid is changed in a wild type LOX, preferably of potato tuber.

In a preferred embodiment, the amino acids are change in the region of the amino acid position 570 to 581 of potato tuber LOX. The above-indicated amino acid positions refer to the sequence under the access number S73865 in the EMBL data base or the sequence according to FIG. 3. The positions in LOXs of other plant species, which correspond to the amino acid positions 593 to 602 of *Cucumis sativus* lipoxygenase, can easily be determined by sequence comparisons between sequence X92890 and the further protein sequences, e.g., of soybean, potato, *arabidopsis*, tobacco or barley. The following Table 1 shows the result of an amino acid comparison between the cucumber-derived enzyme and the corresponding positions in the enzymes of other plants. The first group (15-LOX) shows a comparison between LOXs which at position 15 introduce a hydroperoxy group into an arachidonic acid molecule, while the second group (5-LOX) shows a comparison between sequences which introduce a hydroperoxy group at position 5.

TABLE 1

Comparison of amino acid residues involved in the specificity of a plant LOX for a specific position (15 or 5).

| ENZYME | Access No. | Position of amino acid residue | Amino acid residue |
|---|---|---|---|
| 15-LOX | | | |
| Cucumber lipid body LOX | X92890 | 596/597 | Thr/His |
| Soybean seed LOX-1 | P08170 | 556/557 | Thr/Phe |
| Potato LOX-H1 | X96405 | 614/615 | Ser/Phe |
| *Arabidopsis* LOX-2 | P38418 | 611/612 | Cys/Phe |
| 5-LOX | | | |
| Potato LOX | S73865 | 575/576 | Thr/Val |
| Tobacco elicitor-induced LOX | X84040 | 580/581 | Thr/Val |
| Barley grain LOX-A | L35931 | 574/575 | Thr/Val |

The sequence motif at position 570 to 581 is GVLEST VFPSK (sequence according to S73865).

In a particularly preferred embodiment the exchange takes place at position 576 of sequence S73865. At position 576, there is a Val residue in the wild type. The residue at position 576 is here replaced by a Phe residue. The exchange in the region of the amino acid position 570 to 581 has the effect that the potato tuber 5-LOX is converted to an arachidonic acid 11-LOX. In the following this mutant will also be designated as V576F. The wild type sequence is shown as FIG. 3. Position 576 is marked.

Preferably, the amino acids are exchanged in the wild type with the help of directed mutagenesis, as is sufficiently known in the prior art.

The present invention further relates to LOX mutants which are obtainable according to the above-described methods. The LOXs according to the invention can be produced with the help of the methods known from the prior art, for example directed mutagenesis, and subsequent protein expression. In particular mutants which after incubation with arachidonic acid yield at least 40%, preferably 50%, of the derivative perhydroxylated at position 11 are considered to be inventive.

The present invention further relates to nucleic acids which code for the LOXs according to the invention. Starting from the wild type sequences available in the prior art, the sequences according to the invention can be produced by directed mutagenesis.

Furthermore, the present invention relates to vectors into which the nucleic acids according to the invention are introduced for the purpose of cloning and expression. Corresponding cloning and expression vectors are sufficiently known to the skilled artisan from the prior art (cf. Maniatis et al. Molecular Cloning, A Laboratory Manual (1989), Cold Spring Hator Laboratory Press).

The present invention further relates to a cell into which the nucleic acid according to the invention or the vector according to the invention is introduced. After introduction of the nucleic acid or the vector, the cell is then capable of expressing a LOX for the first time or at a large scale. The fatty acid pattern of a cell can thereby be changed in a targeted way, with the result that the phenotype of the cell can be altered in different respects. This includes, inter alia, a different composition of the cell membrane.

Finally, new plants or plant parts can be regenerated from the above-mentioned cells by in vitro culturing methods. For the production of such transgenic plants the known transformation system can be used, e.g., on the basis of *Agrobacteria* and Ti plasmid derivatives.

The LOXs according to the invention make it possible to produce for the first time new arachidonic acid derivatives at a large scale. To this end, arachidonic acid is incubated as a substrate with the LOXs according to the invention under appropriate conditions. Hydroperoxylation of the arachidonic acid is then effected, preferably at position 11.

Particularly preferred is an arachidonic acid derivative which contains a hydroperoxy group at position 11. The derivative can then easily be converted into the hydroxy derivative. The thus available 11S-HPETE can be used for producing the alcohols, aldehydes and dicarbonic acids shown below. The enzyme hydroperoxide lyase is contained in extracts of cucumber seedlings, for example. 2E- and 3Z-nonenal and their alcohols are important flavorings in foodstuff (e.g., cucumbers).

Such an arachidonic acid derivative has so far not been available because a LOX of an appropriate positional specificity has been missing.

The further examples serve to explain the invention.

1. Preparation of the Mutant V576F

Materials:

The chemicals used were obtained from the following sources: standards of chiral and racemic hydroxy fatty acids were obtained from Chayman Chem (Ann Arbor, Mi, USA). Methanol, hexane, 2-propanol (all HPLC grade) were obtained from Baker (Griesheim, Germany). Restriction enzymes were purchased from New England BioLabs (Schwalbach, Germany).

Directed Mutagenesis and Protein Expression:

For bacterial expression of wild type LOX and LOX mutant and for directed mutagenesis, use was made of the plasmid pet3b (Novagen, Germany) which contained the cDNA of the potato tuber LOX as insert (PET-LOX1; cf. Geerts, A., Feltkamp, D., Rosahl, S. (1994) Expression of lipoxygenase in wounded tubers of *solanum tuberosum* L., Plant Physiol. 105: 269–277). Mutagenesis was carried out by using the QuikChange Mutagenesis Kit from Stratagene (Heidelberg, Germany). Oligonucleotides containing the appropriate base exchanges were purchased from MWG-Biotech (Ebersberg, Germany). To analyze the mutation, an additional conservative base exchange was introduced to construct a new restriction cleavage site. In addition, the mutation was sequenced and at least five different bacterial clones were expressed and used for analyzing the enzymatic characteristics. Expression of pET-LOX1 and its mutant was performed as described by Feussner, I., Bachmann, A., Höhne, M. & Kindl, H. (1998) FEBS Lett. 431, 433–436. Cells from 1 liter cultures were resuspended in 5–7 ml lysis buffer and disrupted by using a sonifier tip with pulses each of 30 seconds, and cellular debris was pelleted.

Activity Assay and Sample Preparation:

For product analysis, 0.9 ml of cell lysates were incubated with 0.9 mM arachidonic acid (final concentration) in 100 mM Tris buffer, pH 7.5, for 30 minutes at room temperature. Reaction was stopped by the addition of sodium borohydride to convert the hydroperoxy fatty acids formed to the corresponding hydroxy compounds. The samples were acidified to pH 3 and the lipids were extracted (cf. Bligh, E. G. & Dyer, W. J. (1959) Can. J. Biochem. Physiol. 37, 911–917). The lower chloroform phase was recovered and the solvent was evaporated. The remaining lipid was dissolved with 0.1 ml methanol, and aliquots were subjected to HPLC analysis.

Analysis:

HPLC analysis was carried out on a Hewlett Packard 1100 HPLC system coupled to a diode detector. RP-HPLC of the free fatty acid derivatives was carried out on a Nucleosil C-18 column (Macherey-Nagel, 250×4 mm, 5 μm particle size) with a solvent system of methanol/water/acetic acid (85/15/0.1; v/v/v) and at a flow rate of 1 ml/min. Absorption at 234 nm (absorption of the conjugated diene system of the hydroxy fatty acids) and at 210 nm (polyenoic fatty acids) was recorded accordingly. Straight-phase HPLC (SP-HPLC) of hydroxy fatty acid isomers was carried out on a Zorbax SIL column (HP, Waldbronn, Germany; 250×4.6 mm, 5 μm particle size) with a solvent system of n-hexane/2-propanol/acetic acid (100/2/0.1, v/v/v) at a flow rate of 1 ml/min. The enantiomer composition of the hydroxy fatty acids was analyzed by chiral-phase HPLC on a Chiralcel OD column (Daicel Chem. Industries, distributed by Baker Chem., Deventer, Netherlands; 250×4.6 mm, 5 μm particle size) with a solvent system of hexane/2-propanol/acetic acid (100/5/0.1, v/v/v) at a flow rate of 1 ml/min. (Cf. Feussner, I., Balkenhohl, T. J., Porzel, A., Kühn, H.& Wasternack, C. (1997) J. Biol. Chem. 272, 21635–21641).

2. Preparation of the LOX-V576F Mutant:

The reagents and methods employed for preparing said mutant were substantially as already described above. A few modifications of the above-mentioned methods which were specifically adapted to the preparation of the V576F mutant are now explained.

Figure 2:
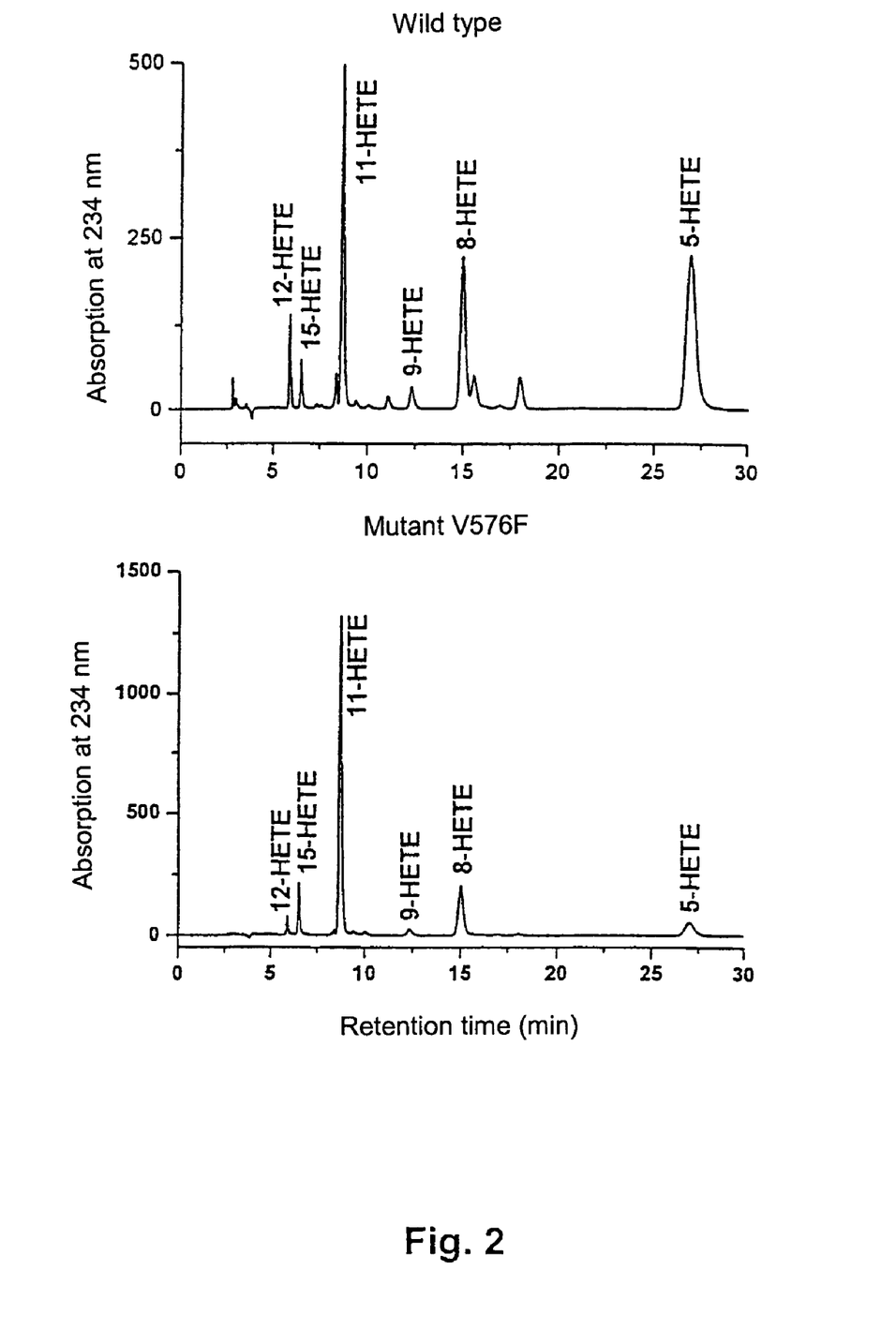
FIG. 2 shows the HPLC analysis of hydroxy fatty acids obtained with the help of wild type LOX of potato tubers and the V576F mutant of arachidonic acid after reduction of hydroperoxy fatty acids with sodium borohydride.

Directed Mutagenesis and Protein Expression:

The starting cDNA and the mutagenesis kit were as described above. For analysis of the mutation further conservative base exchanges were carried out for producing a new restriction cleavage site for BsTBL. The following primers were used for producing the mutation V576F: GCT GGT GGG GTT CTT GAG AGT ACA TTC TTT CCT TCG AAA TTT GCC ATG GAA ATG TCA GCT G (coding strand) [SEQ ID NO:1] and CAG CGT ACA TTT CCA TGG CAA ATT TCG AAG GAA AGA ATG TAC TCT CAA GAA CCC CAC CAG C (complementary strand) [SEQ ID NO:2]. Furthermore, the mutant was sequenced and 5 different bacterial colonies were expressed and used for enzymatic studies. The expression of pET-LOX1 was carried out as described above. The further preparation was carried out as already indicated above. Analysis of the produced fatty acid derivative (containing a hydroperoxy group at position 11) was carried out as indicated above. The result of the SP-HPLC analysis for converting arachidonic acid with V576F is shown in FIG. 2. The following Table 2 shows a comparison of the specificity of the wild type (wtLOX) with the mutant ($LOXV_{576}F$).

TABLE 2

Comparison of the product specificity of wtLOX and $LOXV_{576}F$ with arachidonic acid

| Enzyme | (15S, 13E, 11Z, 8Z,5Z)- 20:4 | (12S, 14Z, 10E, 8Z,5Z)- 20:4 | (11S, 14Z, 12E, 8Z,5Z)- 20:4 | (9S, 14Z, 11Z, 7E,5Z)- 20:4 | (8S, 14Z, 11Z9E, 5Z)- 20:4 | (5S, 14Z, 11Z, 8Z6E)- 20:4 |
|---|---|---|---|---|---|---|
| wtLOX | 5% | 6% | 23% | 3% | 21% | 42% |
| $LOXV_{576}F$ | 9% | 4% | 50% | 3% | 23% | 11% |

3. Description of the Figures

FIG. 1 shows that the positional specificity of the LOX reaction depends on the site of hydrogen cleavage and the orientation of the radical. The [+2] radical arrangement indicates that oxygen is inserted at the second carbon atom in the direction of the methyl terminus of the substrate counted from the site of hydrogen removal. [−2] indicates the inverse orientation of the radical arrangement.

FIG. 2 shows HPLC analysis of fatty acids with the mutant V576F. Equal amounts of LOX protein were incubated with 0.9 mM arachidonic acid at room temperature for 30 minutes. After reduction of lipids with sodium borohydride, the reaction mixture was acidified to pH 3, and the lipids were extracted. Oxygenated fatty acid derivatives were isolated by RP-HPLC, and the individual positional isomers were analyzed by SP-HPLC. Ratios of S and R were determined by HPLC (insets).

Figure 3:
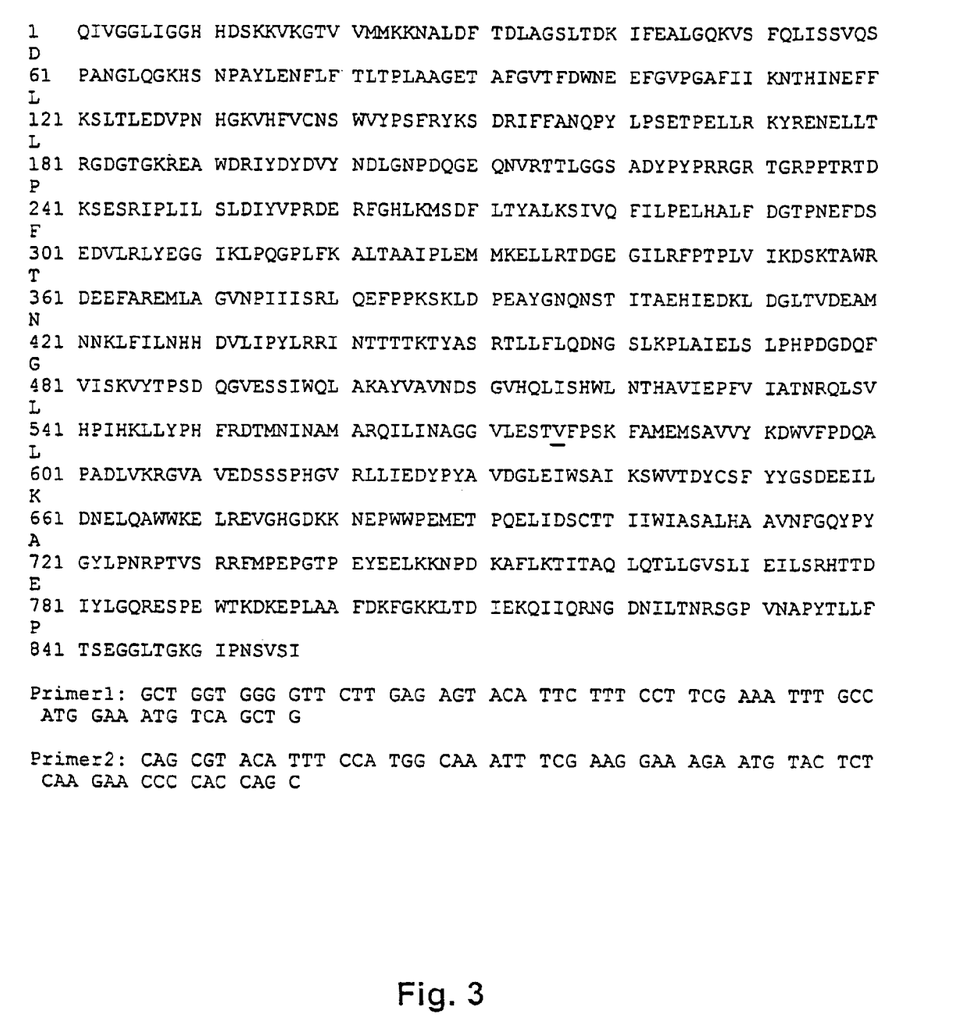
FIG. 3 shows the sequence of wild type LOX of potato tubers [SEQ ID NO:3]. The mutagenized amino acid position is underlined. Primers 1 and 2 [SEQ ID NOS: 1 and 2, respectively] as used are also shown.

FIG. 3 shows the amino acid sequence of the wild type lipoxygenase of potato tubers. The mutated Val576 is underlined.

| Abbreviations used: | |
|---|---|
| CP-HPLC | for chiral-phase HPLC; |
| RP-HPLC | for reverse-phase HPLC; |
| SP-HPLC | for straight-phase HPLC; |
| HPETE | for hydroperoxy arachidonic acid; |
| LOX | for lipoxygenase; |
| HETE | for hydroxy arachidonic acid |

The invention claimed is:

1. A method of enhancing the specificity of a potato tuber lipoxygenase for position 11 of arachidonic acid, wherein the potato tuber lipoxygenase consists of SEQ ID NO: 3, which method comprises changing the amino acid at position 576 of SEQ ID NO: 3 to a Phe residue, whereupon the specificity of the potato tuber lipoxygenase for position 11 of arachidonic acid is enhanced.

2. The method according to claim 1, characterized in that the amino acid change is effected by directed mutagenesis.

3. An isolated or purified lipoxygenase obtained by the method of claim 1.

4. An isolated or purified nucleic acid encoding the lipoxygenase of claim 3.

5. An isolated or purified vector comprising the nucleic acid of claim 4.

6. An isolated cell comprising the nucleic acid of claim 4 and/or a vector comprising said nucleic acid.

* * * * *

SEQUENCE LISTING

```
<160> NUMBER OF SEQ ID NOS: 3

<210> SEQ ID NO 1
<211> LENGTH: 61
<212> TYPE: DNA
<213> ORGANISM: Artificial
<220> FEATURE:
<223> OTHER INFORMATION: Primer

<400> SEQUENCE: 1
gctggtgggg ttcttgagag tacattcttt ccttcgaaat tgccatgga aatgtcagct    60 g                                                                  61

<210> SEQ ID NO 2
<211> LENGTH: 61
<212> TYPE: DNA
<213> ORGANISM: Artificial
<220> FEATURE:
<223> OTHER INFORMATION: Primer

<400> SEQUENCE: 2
cagcgtacat ttccatggca aatttcgaag gaaagaatgt actctcaaga accccaccag    60
c                                                                  61

<210> SEQ ID NO 3
<211> LENGTH: 857
<212> TYPE: PRT
<213> ORGANISM: Solanum tuberosum

<400> SEQUENCE: 3
```

Gln Ile Val Gly Gly Leu Ile Gly Gly His Asp Ser Lys Lys Val
1               5                   10                  15

Lys Gly Thr Val Val Met Met Lys Lys Asn Ala Leu Asp Phe Thr Asp
            20                  25                  30

Leu Ala Gly Ser Leu Thr Asp Lys Ile Phe Glu Ala Leu Gly Gln Lys
        35                  40                  45

Val Ser Phe Gln Leu Ile Ser Ser Val Gln Ser Asp Pro Ala Asn Gly
    50                  55                  60

Leu Gln Gly Lys His Ser Asn Pro Ala Tyr Leu Glu Asn Phe Leu Phe
65                  70                  75                  80

Thr Leu Thr Pro Leu Ala Ala Gly Glu Thr Ala Phe Gly Val Thr Phe
                85                  90                  95

Asp Trp Asn Glu Glu Phe Gly Val Pro Gly Ala Phe Ile Ile Lys Asn
            100                 105                 110

Thr His Ile Asn Glu Phe Phe Leu Lys Ser Leu Thr Leu Glu Asp Val
        115                 120                 125

Pro Asn His Gly Lys Val His Phe Val Cys Asn Ser Trp Val Tyr Pro
    130                 135                 140

Ser Phe Arg Tyr Lys Ser Asp Arg Ile Phe Phe Ala Asn Gln Pro Tyr
145                 150                 155                 160

Leu Pro Ser Glu Thr Pro Glu Leu Leu Arg Lys Tyr Arg Glu Asn Glu
                165                 170                 175

Leu Leu Thr Leu Arg Gly Asp Gly Thr Gly Lys Arg Glu Ala Trp Asp
            180                 185                 190

Arg Ile Tyr Asp Tyr Asp Val Tyr Asn Asp Leu Gly Asn Pro Asp Gln
        195                 200                 205

-continued

Gly Glu Gln Asn Val Arg Thr Thr Leu Gly Gly Ser Ala Asp Tyr Pro
        210                 215                 220

Tyr Pro Arg Arg Gly Arg Thr Gly Arg Pro Pro Thr Arg Thr Asp Pro
225                 230                 235                 240

Lys Ser Glu Ser Arg Ile Pro Leu Ile Leu Ser Leu Asp Ile Tyr Val
                    245                 250                 255

Pro Arg Asp Glu Arg Phe Gly His Leu Lys Met Ser Asp Phe Leu Thr
                260                 265                 270

Tyr Ala Leu Lys Ser Ile Val Gln Phe Ile Leu Pro Glu Leu His Ala
            275                 280                 285

Leu Phe Asp Gly Thr Pro Asn Glu Phe Asp Ser Phe Glu Asp Val Leu
        290                 295                 300

Arg Leu Tyr Glu Gly Gly Ile Lys Leu Pro Gln Gly Pro Leu Phe Lys
305                 310                 315                 320

Ala Leu Thr Ala Ala Ile Pro Leu Glu Met Met Lys Glu Leu Leu Arg
                    325                 330                 335

Thr Asp Gly Glu Gly Ile Leu Arg Phe Pro Thr Pro Leu Val Ile Lys
                340                 345                 350

Asp Ser Lys Thr Ala Trp Arg Thr Asp Glu Gly Phe Ala Arg Glu Met
            355                 360                 365

Leu Ala Gly Val Asn Pro Ile Ile Ile Ser Arg Leu Gln Glu Phe Pro
        370                 375                 380

Pro Lys Ser Lys Leu Asp Pro Glu Ala Tyr Gly Asn Gln Asn Ser Thr
385                 390                 395                 400

Ile Thr Ala Glu His Ile Glu Asp Lys Leu Asp Gly Leu Thr Val Asp
                    405                 410                 415

Glu Ala Met Asn Asn Asn Lys Leu Phe Ile Leu Asn His His Asp Val
                420                 425                 430

Leu Ile Pro Tyr Leu Arg Arg Ile Asn Thr Thr Thr Lys Thr Tyr
            435                 440                 445

Ala Ser Arg Thr Leu Leu Phe Leu Gln Asp Asn Gly Ser Leu Lys Pro
450                 455                 460

Leu Ala Ile Glu Leu Ser Leu Pro His Pro Asp Gly Asp Gln Phe Gly
465                 470                 475                 480

Val Ile Ser Lys Val Tyr Thr Pro Ser Asp Gln Gly Val Glu Ser Ser
                    485                 490                 495

Ile Trp Gln Leu Ala Lys Ala Tyr Val Ala Val Asn Asp Ser Gly Val
                500                 505                 510

His Gln Leu Ile Ser His Trp Leu Asn Thr His Ala Val Ile Glu Pro
            515                 520                 525

Phe Val Ile Ala Thr Asn Arg Gln Leu Ser Val Leu His Pro Ile His
        530                 535                 540

Lys Leu Leu Tyr Pro His Phe Arg Asp Thr Met Asn Ile Asn Ala Met
545                 550                 555                 560

Ala Arg Gln Ile Leu Ile Asn Ala Gly Gly Val Leu Glu Ser Thr Val
                    565                 570                 575

Phe Pro Ser Lys Phe Ala Met Glu Met Ser Ala Val Val Tyr Lys Asp
                580                 585                 590

Trp Val Phe Pro Asp Gln Ala Leu Pro Ala Asp Leu Val Lys Arg Gly
            595                 600                 605

Val Ala Val Glu Asp Ser Ser Ser Pro His Gly Val Arg Leu Leu Ile
        610                 615                 620

Glu Asp Tyr Pro Tyr Ala Val Asp Gly Leu Glu Ile Trp Ser Ala Ile

```
625                 630                 635                 640
Lys Ser Trp Val Thr Asp Tyr Cys Ser Phe Tyr Tyr Gly Ser Asp Glu
                645                 650                 655

Glu Ile Leu Lys Asp Asn Glu Leu Gln Ala Trp Trp Lys Glu Leu Arg
                660                 665                 670

Glu Val Gly His Gly Asp Lys Lys Asn Glu Pro Trp Trp Pro Glu Met
            675                 680                 685

Glu Thr Pro Gln Glu Leu Ile Asp Ser Cys Thr Thr Ile Ile Trp Ile
        690                 695                 700

Ala Ser Ala Leu His Ala Ala Val Asn Phe Gly Gln Tyr Pro Tyr Ala
705                 710                 715                 720

Gly Tyr Leu Pro Asn Arg Pro Thr Val Ser Arg Arg Phe Met Pro Glu
                725                 730                 735

Pro Gly Thr Pro Glu Tyr Glu Glu Leu Lys Lys Asn Pro Asp Lys Ala
                740                 745                 750

Phe Leu Lys Thr Ile Thr Ala Gln Leu Gln Thr Leu Leu Gly Val Ser
                755                 760                 765

Leu Ile Glu Ile Leu Ser Arg His Thr Thr Asp Glu Ile Tyr Leu Gly
    770                 775                 780

Gln Arg Glu Ser Pro Glu Trp Thr Lys Asp Lys Glu Pro Leu Ala Ala
785                 790                 795                 800

Phe Asp Lys Phe Gly Lys Lys Leu Thr Asp Ile Glu Lys Gln Ile Ile
                805                 810                 815

Gln Arg Asn Gly Asp Asn Ile Leu Thr Asn Arg Ser Gly Pro Val Asn
                820                 825                 830

Ala Pro Tyr Thr Leu Leu Phe Pro Thr Ser Glu Gly Gly Leu Thr Gly
            835                 840                 845

Lys Gly Ile Pro Asn Ser Val Ser Ile
            850                 855
```